(12) United States Patent
Samec et al.

(10) Patent No.: US 10,150,790 B2
(45) Date of Patent: Dec. 11, 2018

(54) DEPOLYMERISATION OF LIGNIN IN BIOMASS

(71) Applicant: KAT2BIZ AB, Stockholm (SE)

(72) Inventors: Joseph Samec, Spånga (SE); Maxim Galkin, Uppsala (SE)

(73) Assignee: Kat2Biz AB, Stockholm (SE)

( * ) Notice: Subject to any disclaimer, the term of this patent is extended or adjusted under 35 U.S.C. 154(b) by 0 days.

(21) Appl. No.: 15/039,165

(22) PCT Filed: Nov. 27, 2014

(86) PCT No.: PCT/SE2014/051416
§ 371 (c)(1),
(2) Date: May 25, 2016

(87) PCT Pub. No.: WO2015/080660
PCT Pub. Date: Jun. 4, 2015

(65) Prior Publication Data
US 2017/0152278 A1 Jun. 1, 2017

(30) Foreign Application Priority Data

Nov. 27, 2013 (SE) ........................................ 1351410

(51) Int. Cl.
*C07G 1/00* (2011.01)
*C08H 7/00* (2011.01)
(Continued)

(52) U.S. Cl.
CPC ................. *C07G 1/00* (2013.01); *C07C 41/01* (2013.01); *C08H 6/00* (2013.01); *C08H 8/00* (2013.01);
(Continued)

(58) Field of Classification Search
CPC .......... C07G 1/00; C07C 41/01; C10G 1/002; C10G 1/086; C10G 2300/1014
See application file for complete search history.

(56) References Cited

U.S. PATENT DOCUMENTS 4,647,704 A * 3/1987 Engel ...................... C07C 37/52
568/716
5,959,167 A * 9/1999 Shabtai .................. C10G 1/002
585/240
(Continued)

FOREIGN PATENT DOCUMENTS

CN 101768052 A 7/2010
CN 102548935 A 7/2012
(Continued)

OTHER PUBLICATIONS

Lu, Qiang, et al. "Catalytic upgrading of biomass fast pyrolysis vapors with Pd/SBA-15 catalysts." Industrial & Engineering Chemistry Research 49.6 (2010): 2573-2580.*
(Continued)

*Primary Examiner* — Nicholas E Hill
(74) *Attorney, Agent, or Firm* — Harness, Dickey & Pierce, P.L.C.

(57) ABSTRACT

A method of obtaining depolymerized lignin from biomass using a transition metal catalyst and a solvent mixture of organic solvent and water. The invention further relates to a composition obtainable by the method and the production of fuel.

17 Claims, 5 Drawing Sheets

(51) Int. Cl.
*C10L 1/02* (2006.01)
*C08H 8/00* (2010.01)
*C08L 97/00* (2006.01)
*C07C 41/01* (2006.01)
*C10G 1/00* (2006.01)
*C10G 1/08* (2006.01)

(52) U.S. Cl.
CPC .......... *C08L 97/005* (2013.01); *C10G 1/002* (2013.01); *C10G 1/08* (2013.01); *C10G 1/083* (2013.01); *C10G 1/086* (2013.01); *C10L 1/02* (2013.01); *C10G 2300/1014* (2013.01); *Y02P 30/20* (2015.11)

(56) References Cited

U.S. PATENT DOCUMENTS

| | | |
|---|---|---|
| 2012/0005949 A1 | 1/2012 | Stevens |
| 2013/0025191 A1 | 1/2013 | Chen et al. |
| 2013/0060071 A1* | 3/2013 | Delledonne ............. C07C 37/54 585/310 |
| 2013/0192123 A1 | 8/2013 | Maschmeyer et al. |
| 2013/0232852 A1 | 9/2013 | Peterson et al. |

FOREIGN PATENT DOCUMENTS

| | | | |
|---|---|---|---|
| WO | WO-2008157164 A1 | 12/2008 | |
| WO | 2009037281 S2 | 3/2009 | |
| WO | WO-2011003029 A2 | 1/2011 | |
| WO | WO-2011117705 A2 * | 9/2011 | ............. C07C 37/54 |
| WO | WO-2012177138 A1 * | 12/2012 | ............... C08H 6/00 |

OTHER PUBLICATIONS

Ye, Yueyuan, et al. "Novel method for production of phenolics by combining lignin extraction with lignin depolymerization in aqueous ethanol." Industrial & Engineering Chemistry Research 51.1 (2011): 103-110.*

Galkin, Maxim V., and Joseph SM Samec. "Selective Route to 2-Propenyl Aryls Directly from Wood by a Tandem Organosolv and Palladium-Catalysed Transfer Hydrogenolysis." ChemSusChem 7.8 (2014): 2154-2158.*

Werhan, Holger, et al. "Acidic oxidation of kraft lignin into aromatic monomers catalyzed by transition metal salts." Holzforschung 65.5 (2011): 703-709.*

Li, Jiebing, Gunnar Henriksson, and Göran Gellerstedt. "Lignin depolymerization/repolymerization and its critical role for delignification of aspen wood by steam explosion." Bioresource technology 98.16 (2007): 3061-3068.*

International Search Report regarding Application No. PCT/SE2014/051416, dated Feb. 27, 2015.

Written Opinion regarding Application No. PCT/SE2014/051416, dated Feb. 27, 2015.

Kirk M Torr et al. (Mild hydrogenolysis of in-situ and isolated Pinus radiata lignins), Bioresource Techn., Elsevier BV, GB, vol. 102 (2011).

* cited by examiner

DEPOLYMERISATION OF LIGNIN IN BIOMASS

CROSS REFERENCE TO RELATED APPLICATIONS

This application is a U.S. National Phase under 35 U.S.C. 371 of International Application No. PCT/SE2014/051416, filed Nov. 27, 2014, and published in English as WO 2015/080660 A1 on Jun. 4, 2015. This application is based on and claims priority to Swedish Application No. 1351410-4, filed Nov. 27, 2013. The entire disclosures of the above applications are incorporated herein by reference.

FIELD OF THE INVENTION

The present invention relates to a method of depolymerizing lignin from biomass using a transition metal catalyst. The present invention facilitates an integration of depolymerisation of lignin into a pulping process.

BACKGROUND

There is an increasing interest in using biomass as a source for fuel production or fine chemical production. Biomass includes, but is not limited to, plant parts, fruits, vegetables, processing waste, wood chips, chaff, grain, grasses, corn, corn husks, weeds, aquatic plants, hay, paper, paper products, recycled paper and paper products, lignocellulosic material, lignin and any cellulose containing biological material or material of biological origin.

An important component of biomass is the lignin present in the solid portions of the biomass. Lignin comprises chains of aromatic and oxygenate constituents forming larger molecules that are not easily treated. A major reason for difficulty in treating the lignin is the inability to disperse the lignin for contact with catalysts that can break the lignin down.

Lignin is one of the most abundant natural polymers on earth. One common way of obtaining lignin is by separation from wood during pulping processes. Only a small amount (1-2%) is utilized in specialty products whereas the rest primary serves as fuel. Even if burning lignin is a valuable way to reduce usage of fossil fuel, lignin has significant potential as raw material for the sustainable production of chemicals and fuel.

Various lignins differ structurally depending on raw material source and subsequent processing, but one common feature is a backbone consisting of various substituted phenyl propane units that are bound to each other via aryl ether or carbon-carbon linkages. They are typically substituted with methoxyl groups and the phenolic and aliphatic hydroxyl groups provide sites for e.g. further functionalization. Lignin is known to have a low ability to sorb water compared to for example the hydrophilic cellulose.

Today lignin may be used as a component in for example pellet fuel as a binder but it may also be used itself as an energy source due to its high energy content. Lignin has higher energy content than cellulose or hemicelluloses and one gram of lignin has on average 2.27 KJ, which is 30% more than the energy content of cellulosic carbohydrate. The energy content of lignin is similar to that of coal. Today, due to its fuel value lignin that has been removed using the kraft process, sulphate process, in a pulp or paper mill, is usually burned in order to provide energy to run the production process and to recover the chemicals from the cooking liquor.

Lignin depolymerisation (LDP) is a key step for its efficient utilization. Efficient LDP process should lead to new green starting materials for bulk and fine chemical industries. Also LDP process followed by a hydrodeoxygenation (HDO) step will be a straight road toward fossil fuels substitutes. Among all proposed methods for lignin depolymerisation a redox neutral pathway that requires no external hydrogen source is the most economical. The chemical structure of the lignin is very complicated, where the β-O-4'-glycerolaryl ether linkage represents the most common repeating monomeric unit in organosolv and enzymatic hydrolysis lignin.

Biofuel, such as biogasoline and biodiesel, is a fuel in which the energy is mainly derived from biomass material or gases such as wood, corn, sugarcane, animal fat, vegetable oils and so on. However the biofuel industries are struggling with issues like food vs fuel debate, efficiency and the general supply of raw material. At the same time the pulp or paper making industries produces huge amounts of lignin which is often, as described above, only burned in the mill. Two common strategies for exploring biomass as a fuel or fuel component are to use pyrolysis oils or hydrogenated lignin.

One drawback of using lignin as a source for fuel production is the issue of providing lignin or lignin derivatives in a form suitable for hydro treaters or crackers. The problem is that lignin is not soluble in oils or fatty acids which is, if not necessary, highly wanted.

Prior art provides various strategies for degrading lignin into small units or molecules in order to prepare processable lignin derivatives. These strategies include hydrogenation, deoxygenation and acid catalyst hydrolysis. WO2011003029 relates to a method for catalytic cleavage of carbon-carbon bonds and carbon-oxygen bonds in lignin. US20130025191 relates to a depolymerisation and deoxygenation method where lignin is treated with hydrogen together with a catalyst in an aromatic containing solvent. All these strategies relates to methods where the degradation is performed prior to eventual mixing in fatty acids or oils. WO2008157164 discloses an alternative strategy where a first dispersion agent is used to form a biomass suspension to obtain a better contact with the catalyst. These strategies usually also requires isolation of the degradation products in order to separate them from unwanted reagents such as solvents or catalysts.

The economics in producing fuels or fine chemicals from biomass depend for example on an efficient process for preparing the lignin and on the preparation of the lignin or lignin derivatives so that the fuel production is as efficient as possible. For example the amount oxygen should be as low as possible and the number of preparation steps should be as few as possible.

SUMMARY OF THE INVENTION

The object of the present invention is to provide a method of preparing depolymerized lignin from a biomass feedstock.

A first aspect of the present invention relates to a composition comprising a solvent and one or more compounds having the formula of:

wherein each R1 and R2 is H or OCH$_3$ and R3 is (CH$_2$)$_2$CH$_3$, (CH$_2$)$_3$CH or (CH)$_2$CH$_3$ and wherein at least one of the compounds is A second aspect of the present invention relates to a method of preparing the composition by depolymerizing lignin comprising
  a. Providing biomass in particulate form, the biomass containing lignin, a solvent mixture comprising an organic solvent and water, and a transition metal catalyst;
  b. Mixing the biomass, the solvent mixture and the transition metal catalyst to obtain a mixture;
  c. Heating the mixture to at least 80° C.; and
  d. Optionally isolating the depolymerized lignin.

A third aspect of the present invention relates to depolymerized lignin obtainable by the method according to the present invention.

Another aspect of the present invention relates to a method of producing one or more compounds having the formula of:

wherein each R1 and R2 is H or OCH$_3$ and R3 is (CH$_2$)$_2$CH$_3$, (CH$_2$)$_3$OH or (CH)$_2$CH$_3$ comprising:
  a. Providing biomass in particulate form, the biomass containing lignin, a solvent mixture comprising an organic solvent and water, and a transition metal catalyst;
  b. Mixing the biomass, the solvent mixture and the transition metal catalyst to obtain a mixture;
  c. Heating the mixture to at least 80° C.; and
  d. Optionally isolating the one or more compounds.

Yet another aspect of the present invention relates to the use of the composition of the present invention for fuel production.

Yet another aspect of the present invention relates to a method of making fuel comprising cracking or hydro treating compounds according to the present invention in a refinery.

Yet another aspect of the present invention relates to a method of producing one or more compounds having the formula of:

wherein each R1 and R2 is H or OCH$_3$ and R3 is (CH$_2$)$_2$CH$_3$, (CH$_2$)$_3$OH or (CH)$_2$CH$_3$ comprising:
  a. Providing biomass in particulate form wherein the biomass contains lignin, a solvent mixture comprising an organic solvent and water, and a transition metal catalyst;
  b. Mixing the biomass, the solvent mixture and the transition metal catalyst to obtain a mixture;
  c. Heating the mixture to at least 80° C. and depolymerize the lignin at a pressure of not more than 50 bar, preferably 35 bar or less; and
  d. Optionally isolating the depolymerized lignin.

DETAILED DESCRIPTION OF THE INVENTION

The present invention provides a straight forward method of depolymerizing lignin direct from the biomass, without first isolating the lignin. The method according to the present invention makes the lignin more soluble and more lignin may be extracted from the biomass. Furthermore, the method may be implemented into the already existing techniques such as the organosolv process.

The method of the present invention does not involve the use of an added hydrogen donor such as formic acid. In the method according to the present invention an alcohol is not a hydrogen donor, or it is not at least the major hydrogen donor. Instead without being bound by theory it is believed that the hydrogen needed to depolymerize the lignin comes from the biomass itself.

A desirable feature of the refinery feedstock is a low oxygen content or as low oxygen to carbon ratio as possible. The composition obtained by the present invention is believed to be a suitable feedstock for refinery since it may be dissolved in various solvents, including oils and fatty acids, and has a low oxygen to carbon content.

Biomass includes, but is not limited to wood, fruits, vegetables, processing waste, chaff, grain, grasses, corn, corn husks, weeds, aquatic plants, hay, paper, paper products, recycled paper, shell, algae, straw, bark or nut shells, lignocellulosic material and any cellulose containing biological material or material of biological origin. In one embodiment the biomass is wood, preferably particulate wood such as saw dust or wood chips. The wood may be any kind of wood, hard or soft wood, coniferous tree or broadleaf tree. A non-limiting list of woods would be pine, birch, spruce, maple, ash, mountain ash, redwood, alder, elm, oak and beech. The present inventors have found that the depolymerization of the lignin according to the present invention is much more effective if the lignin is not chemically pre-treated or modified for example reduced or oxidized. For example kraft lignin or lignosulfonate treated according to the present invention will be less depolymerized in comparison with saw dust or wood chips or organosolv lignin treated with the method according to the present invention. In one embodiment the biomass contains lignin where the chemical structure or chemical composition of the lignin has essentially not been modified. In one embodiment the biomass is organosolv lignin, i.e. lignin obtained from an organosolv process.

In the present application the term "lignin derivative" means molecules or polymers derived from lignin. In the present application "lignin derivative" and "molecules or polymers derived from lignin" are used interchangeably. These molecules or polymers may be a result of chemical modification or degradation of lignin or a lignin source, for example when treating black or red liquor in order to precipitate or separate lignin.

Figure 1:
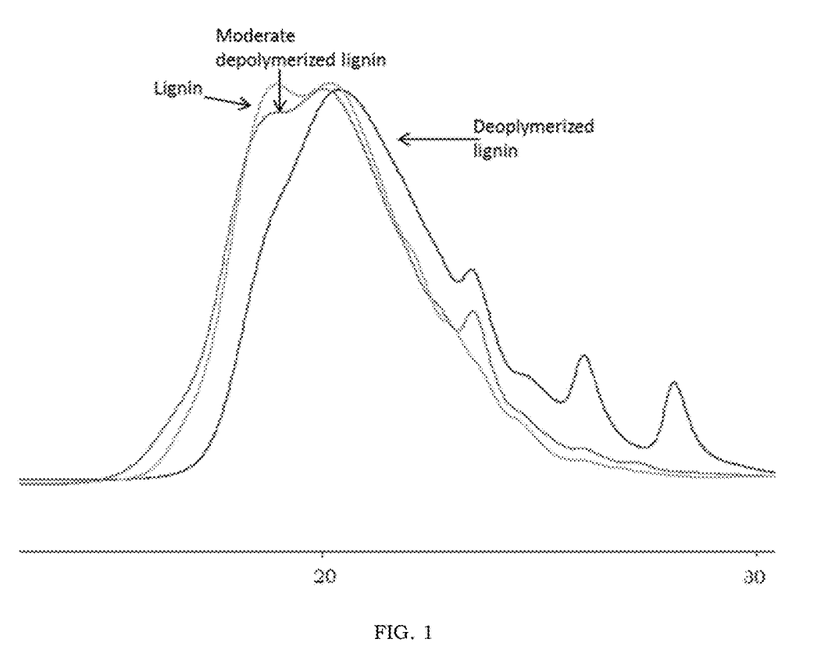
FIG. 1. GPC chromatogram for lignin, moderate depolymerized lignin and depolymerized lignin.

What the present inventors found was that even though the addition of a hydrogen donor (such as formic acid) resulted in selective cleavage of the β-o-4 bond in a model studies and depolymerization of the model polymer (Example 1), the conditions used did not result in any depolymerization of lignin, even at 160° C. When reacting lignin with Pd/C (5 mol %), sodium borohydride (10 mol %) in water/ethyl acetate at 160° C. for 1 h at autogenous pressure the treatment lead only to moderate depolymerization, see FIG. 1.

Instead the inventors took advantage of the conditions used during organosolv treatment of biomass. Organosolv is a pulping technique originating from the early 1930's while the main development was performed during the late 1980's where biomass is separated in cellulose and, lignin and hemicellulose. The technique involves contacting a lignocellulosic feedstock such as chipped wood with an aqueous organic solvent at temperatures ranging from 140° C. and higher usually not higher than 220° C. This causes hydrolytic depolymerization of alpha aryl-ether links into fragments that are soluble in the organic solvent. Solvents used include acetone, methanol, ethanol, butanol, ethylene glycol, formic acid, and acetic acid. The concentration of the solvent in water may be in the range of 40 to 80 wt %. Higher boiling solvents may be used and have the advantage that a lower process pressure may be used, on the other hand such solvents are harder to recover. The organosolv process may be a two or more-stage process where the same or different solvents are used in the two stages. A base such as sodium hydroxide may be added, preferably in the second stage and the lignin may be isolate by lowering the pH using any suitable acid. In order to isolate the high molecular weight lignin from hemicellulose in the organosolv process the lignin may be precipitated or the mixture may be filtrated, evaporated, distilled or centrifuged.

By treating the biomass, for example wood chips or sawdust, in an organic solvent in the presence of a transition metal catalyst at an elevated temperature the present inventors found that the obtained depolymerized lignin had a molecular weight of less than 900 g/mol while the control method lacking the catalyst resulted in lignin having a molecular weight of 6000 g/mol. The present invention may easily be integrated into a pulping process involving an organosolv process leaving not only depolymerized lignin but also high quality cellulose and hemi cellulose.

The depolymerized lignin comprises compounds having the formula of:

wherein each R1 and R2 is H or $OCH_3$ and R3 is $(CH_2)_2CH_3$, $(CH_2)_3OH$ or $(CH)_2CH_3$. Specific examples of said compounds are wherein 1 is guaiacylpropane, 2 is guaiacylpropanol, 3 is syringylpropane, 4 is syringylpropanol and 5 is 2-methoxy-4-(prop-1-enyl)phenol. The method of the present invention generates a mixture of compounds. Mainly, the method results in compound 5 and only low contents of compounds 3 and 4 and thereby the compounds obtained by the present invention and the composition according to the present invention have a low oxygen to carbon ratio. In one embodiment the generated mixture comprises less than 10 mol % of each compound 1 to 4 and more than 50 mol % of compound 5. In one embodiment the generated mixture comprises less than 5 mol % of each compound 1 to 4 and more than 70 mol % of compound 5, or the generated mixture comprises less than 5 mol % of compounds 1 to 4 and more than 80 mol % of compound 5. In one embodiment the mixture comprises 1-10 wt % of compound 1 to 4. In another embodiment the mixture comprises 70-90 wt % of compound 5. A higher degree of compound 5 may be beneficial since it has a low oxygen to carbon ratio and also a higher selectivity results in a mixture which is more predictable concerning further treatments and thereby easier to refine.

In one embodiment the biomass is a biomass which contains lignin, preferably wood, and wherein the biomass is particulate biomass such as saw dust or wood chips. The biomass may be ground to small size particles or powder using any suitable technique. The size of the particles may be 10 cm or less, or 5 cm or less, or 2 cm or less, or 5 mm or less, or 1 mm or less, or 500 µm or less.

The biomass is mixed with an organic solvent or a mixture comprising at least one organic solvent. In one embodiment a solvent mixture comprising an organic solvent and water is used. The organic solvent may be an oxygenate such as an alcohol, ester, ketone, ether or furane or furfural based solvent. Preferred solvents are C1-C10 alcohols, C2-C10 ethers, C2-C10 carboxylic acids, C3-C10 ketones and C2-C10 esters, for example methanol, ethanol, propanol, isopropanol, butanol, glycerol, acetone and butyl ether such as tert-butyl methyl ether; diethyl ether, diglyme, diisopropyl ether, dimethoxyethane, diethylene glycol diethyl ether, polyethylene glycol 1,4-dioxane, acetic acid, and tetrahydrofuran. In one embodiment the solvent is selected from water, methanol, ethanol, butanol, propanol or acetone or a combination thereof. Preferred C1-C10 esters are organic esters, aromatic or non-aromatic esters, examples of esters are benzyl benzoate, various acetates such as methyl acetate, ethyl acetate and butyl acetate, various lactates such as ethyl lactates. In one embodiment the solvent comprises a combination of C1-C10 alcohols, C2-C10 ethers, C2-C10 carboxylic acids and C2-C10 esters. In one embodiment the solvent comprises two C1-C10 alcohols for example ethanol and glycerol, and in another embodiment the solvent comprises propanol and glycerol. In one embodiment the solvent comprises polyethylene glycol and a C1-C10 alcohol. In one embodiment the solvent comprises furfural or furfuryl alcohol. When the solvent is a mixture of an organic solvent and water the mixture may contain methanol and water, ethanol and water, isopropanol and water, acetic acid and water or ethyl acetate and water, preferably ethanol and water, isopropanol and water and methanol and water. The ratio between the organic solvent and water may be from 1:10 to 10:1 (organic solvent:water weight ratio), such as 1:8 to 8:1 preferably 1:4 to 4:1, or 1:2 to 2:1 preferably around 1:1. In one embodiment the solvent mixture comprises 40-60 weight % of organic solvent and 40-60 weight % of water. The substrate, or biomass, concentration in the solvent may be 0.1 wt % or more, or 0.5 wt % or more, or 1 wt % or more, or 2 wt % or more, or 5 wt % or more, or 10 wt % or more, or 20 wt % or more, or 30 wt % or more and may be 70 wt % or less or 50 wt % or less.

The method may be performed without water, for example by using only an organic solvent, but by adding water the method becomes more suitable for large scale production due to the reduced risk of explosions. There is no need to add any base or any additional base to the reaction.

A transition metal catalyst is used to treat the biomass and the transition metal may be selected from or based on but not limited to palladium (Pd), platinum (Pt), ruthenium (Ru), rhodium (Rh) nickel (Ni), iron (Fe), copper (Cu), chromium (Cr), molybdenum (Mo), tungsten (W), preferably Pd, Pt, Fe, Ni or Cu. In one embodiment the catalyst is Pd. In one embodiment the catalyst is Pt. In one embodiment the catalyst is W or W/C. In one embodiment the catalyst is Fe. In one embodiment the catalyst is Ni based such as Raney Nickel. In one embodiment the catalyst is Cu. The catalyst may also be a combination of said metals or bi-metallic catalyst comprising at least one of said metals. In another embodiment the catalyst is a palladium and/or platinum doped metal catalyst. The doped metal catalyst may be a copper, nickel or iron based catalyst which has been doped with palladium or platinum. The catalyst may be in the form of a powder, grains, coated surface or a solid material. In one embodiment the catalyst is selected from Pd, $Pd_2(dba)_3$ (Tris(dibenzylideneacetone)dipalladium(0)), $Pd(OAc)_2$ (Palladium(II) acetate), $Pd(PPh_3)_4$ (Tetrakis(triphenylphosphine)palladium(0)), $Pd(P^tBu_3)_2$ (Bis(tri-tert-butylphosphine)palladium(0)) or Pd/C (Palladium on charcoal). In another embodiment the catalyst is Pt, platinum black or $PtO_2$. In another embodiment the catalyst is Rh/C. In another embodiment the catalyst is Ru/C. The catalyst may be pre-activated prior to use for example by removal of oxygen or oxides through the use of a reducing agent. The catalyst may be added in at least catalytic amounts. In one embodiment the amount of catalyst is 0.5 mol % or more, or 1 mol % or more, or 3 mol % or more, or 5 mol % or more, or 7 mol % or more, or 10 mol % or more, or 100 mol % or less, or 50 mol % or less, or 25 mol % or less, or 15 mol % or less, or 12 mol % or less, in relation to the lignin content. It is believed that when using Pd or Pt based catalysts or catalysts doped with Pd or Pt the method becomes insensitive or at least less sensitive to water. It is preferred that the catalyst is in contact with the substrate or the biomass during the reaction.

The biomass and the catalyst forms a slurry or a mixture in the solvent and the mixture is heated to at least 80° C., or at least 120° C., preferably 130° C. or higher, or 140° C. or higher, or 150° C. or higher, or 160° C. or higher, or 170° C. or higher, or 180° C. or higher, or 190° C. or higher, or 250° C. or lower, or 230° C. or lower, or 210° C. or lower, or 200° C. or lower. The treatment time is dependent on the solvent used and the volume to be treated. As an example the mixture of biomass and catalyst in the solvent, may be heated during 30 minutes or more, or 1 hour or more, or 1.5 hours or more, or 2 hours or more when treating a volume of 3 ml. The treatment, or the reaction, is fast and may be terminated after 1 hour or less, or after 3 hours or less, or after 10 hours or less.

The reaction may be performed in a closed or sealed container creating an autogenous pressure. The reaction is preferably conducted during continuous mixing. The pressure during the depolymerization may be around 100 bar or less, or 50 bar or less, or 45 bar or less, or 35 bar or less, or 25 bar or less, or 10 bar or less, for example 8 bar or less, or 5 bar or less, or 2 bar or less, or 1 bar or more. In one embodiment the pressure during the depolymerization is 5-45 bar, such as 20-35 bar. However one major advantage of the present invention is that no hydrogen gas is needed. The reaction may also be performed during reflux.

The treatment, or reaction, may be performed in air, or in an atmosphere with reduced oxygen pressure, or in an inert atmosphere such as nitrogen or argon. When a palladium catalyst is used the use of an inert atmosphere gives better results but is not necessary.

After the treatment the depolymerized lignin may be isolated by filtration, evaporation, distillation or centrifugation or any suitable technique. It is believed that the cellulose or the hemi-cellulose will not be affected or at least only slightly depolymerized. This makes the present invention also an interesting method for producing high quality pulp and hemi-cellulose. By first treating the lignocellulosic feedstock according to organosolv processes followed by the method according to the present invention, high quality pulp and hemi-cellulose as well as depolymerized lignin may be obtained.

The obtained depolymerized lignin has a weight average molecular weight ($M_w$) of less than 1500 g/mol, or preferably less than 1200 g/mol, or less than 900 g/mol. In one embodiment 80% or more of the obtained lignin has a molecular weight of less than 600 g/mol, or less than 400 g/mol. In one embodiment 2-methoxy-4-(prop-1-enyl)phenol in 15% yield or more, or 20% yield or more is obtained.

By separating and recycling the catalyst the process becomes more efficient and even more economically favorable. The catalyst may be used several times before losing in reactivity. The reactivation may be done by treating the catalyst with hydrogen. For example the catalyst may be placed in alcohol such as ethanol and left for several hours (2-15 hours for example) under hydrogen pressure (3-6 bar for example). The reactivation may be performed at room temperature (20° C.) and the reactivated catalyst may be rinsed with an alcohol for example ethanol.

The depolymerized lignin, or the compounds, obtained by the method of the present invention, and especially the compounds having the formula wherein each R1 and R2 is H or $OCH_3$ and R3 is $(CH_2)_2CH_3$, $(CH_2)_3OH$ or $(CH_2)_2CH_3$ may be used to make fuel. The compounds may be in the form of a composition comprising a solvent and an additive where the solvent may be a fatty acid or an oil. In one embodiment the compounds (the depolymerized lignin) in the composition make up 5-30 wt % of the composition, or 10-25 wt %. In one embodiment at least 15 wt % of the compounds in the composition is 2-methoxy-4-(prop-1-enyl)phenol, or at least 20 wt %. In one embodiment the content of 2-methoxy-4-(prop-1-enyl) phenol is 10-25 wt %, or 15-20 wt %. The amount 2-methoxy-4-(prop-1-enyl)phenol may be higher, 30-50 wt %, if hard wood is used as biomass.

The compounds or composition according to the present invention may be hydro treated or cracked at a refinery to produce fuel using well known techniques. Furthermore the compounds may be used for preparing fine chemicals such as phenols.

EXAMPLES

Example 1

Preliminary studies showed that β-O-4'-ethanolaryl ethers (50 mg) undergo a slow oxidation of the benzyl hydroxyl group without cleavage to generate the dimeric ketone in the presence of catalytic amounts of Pd/C (5 mol %) and air (Table 1, entry 1), 3 ml of ethyl acetate:water (ratio 3:1). When the reaction was performed under inert atmosphere at 80° C., a very slow transformation toward the desired oxidized and cleaved products was observed (Table 1, entry 2). We found that addition of catalytic amount of hydride or hydrogen donors had an effect on the reaction. Running the Pd/C catalysed aerobic oxidative cleavage reaction in the presence of sodium borohydride, a quantative yield of the desired acetophenone and phenol was achieved within 40 minutes. Several hydrogen donors were screened.

TABLE 1

| Entry | [H]-donor | Oxidation (%) | Cleavage (%) |
|---|---|---|---|
| 1[a] | No | 5 | 0 |
| 2[b,c] | No | 0 | 11 |
| 3[a] | HCOOH | 15 | 35 |
| 4[a] | $NH_4COOH$ | 13 | 32 |
| 5[c] | 2-propanol | 0 | 0 |
| 6[a] | $NaBH_4$ | 0 | 99 |
| 7[b,c] | $NaBH_4$ | 0 | 0 |

[a] Reaction runs under air for 40 min.
[b] Reaction runs under argon atmosphere.
[c] Reaction runs for 24 h instead of 40 min.
Yields were determined by $^1H$ NMR using mesitylene as internal standard.

The degree of methoxylation of lignin aryls depend on its origin. The substrates' substitution (Table 2) mimics the substitution pattern present in switchgrass, soft (pine, spruce, etc.) and hard wood (birch etc.). The reactions gave the corresponding cleaved products in near quantitative yields at 80° C. For highly substituted substrates the reaction proceeded slower and longer reaction time was needed to achieve full conversion.

TABLE 2

| Substrate | R3 | R4 | R3' | R5' | Yield, % |
|---|---|---|---|---|---|
| 1 | H | H | H | H | 95 |
| 2 | H | H | OMe | H | 94 |
| 3 | H | H | OMe | OMe | 97 |
| 4 | H | OMe | H | H | 98 |
| 5 | H | OMe | OMe | H | 98† |
| 6 | H | OMe | OMe | OMe | 94$^a$ |
| 7 | OMe | OMe | H | H | 95$^a$ |
| 8 | OMe | OMe | OMe | H | 98$^a$ |
| 9 | OMe | OMe | OMe | OMe | 92$^a$ |
| 10 | OMe | OH | OMe | H | 96$^a$ |
| 11 | H | OH | OMe | H | 97$^a$ |

$^a$Reaction runs for 4 h instead of 40 min. Average isolated yield of the corresponding ketone based on two duplicate experiments. See (S.I.).

The next step toward lignin depolymerisation was to apply the method to a model polymer to reflect the physical properties e.g. solubility. Model polymer underwent Pd/C catalysed β-O-4' bond cleavage reaction upon treatment at the same conditions as the dimeric models.

The stability of our system in both acidic and basic media should also be taken into account, since produced lignins comprise considerable amounts of acids or base, depending on the processes used, in other words it is insensitive to pH. In the presence of 1M HCl or NaOH the results were identical to neutral conditions. Interestingly if NaOH reaction without palladium hasn't led to any transformation of starting material, in the case of HCl numerous unidentifiable products with a small amount of guaicol were formed (see S.I.). This means that catalytic amounts of palladium could protect lignin from post extraction re-condensation. The results obtained were encouraging and suggested that Pd/C catalyzed depolymerization might be applicable for degradation of plant-derived lignin.

However, lignin under identical conditions did not undergo depolymerization. When reacting lignin with Pd/C (5 mol %), sodium borohydride (10 mol %) in water/ethyl acetate at 160° C. for 1 h at autogenous pressure lead only to moderate depolymerization, FIG. 1.

Example 2

Pine (*Pinus sylvestris*) sawdust (10 g) was mixed with an ethanol water (100 ml, 1:1 ratio) mixture in the presence of Pd/C (5 mol % on lignin content) and heated at 195° C. for 1 h. A control experiment, in which Pd/C was absent, was also performed.

Figure 2:
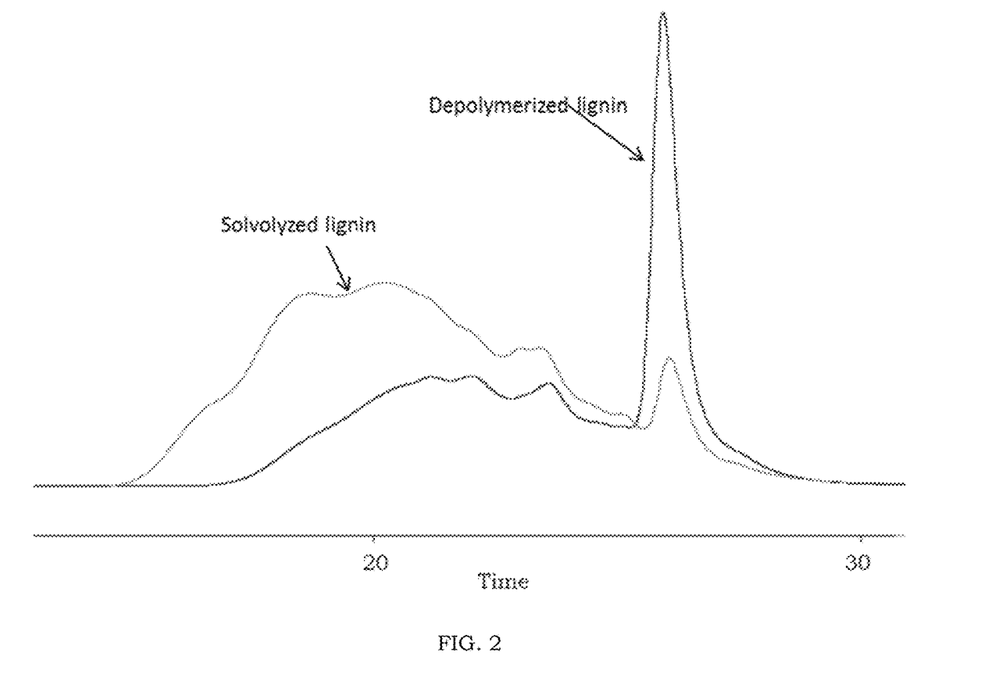
FIG. 2. GPC chromatogram for lignin depolymerized according to the present invention and solvolysed lignin without palladium catalysis.

GPC analysis showed that all lignin obtained was less than Mw 900 Da with more than 80% of the analyt belong to monomers and dimers (less than Mw 400 Da) (Control 6000 Da to 1000 Da 40% of all), FIG. 2. Both NMR and GC/MC analysis showed the presence of one major product, 2-methoxy-4-(prop-1-enyl)phenol. Purification of the oil obtained lead to a 28% yield.

Example 3

Figure 3:
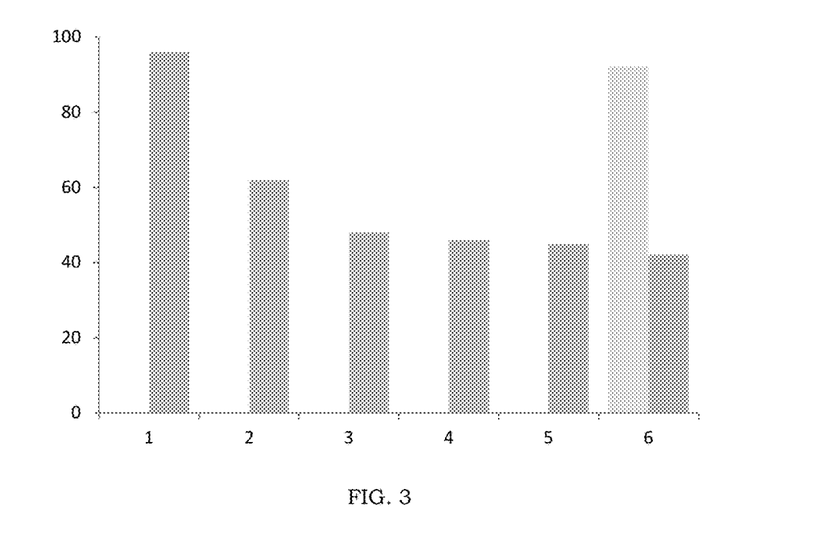
FIG. 3. Recycling of Pd/C in the transfer hydrogenolysis of β-O-4' ethanolaryl ethers. Reaction conditions: 80° C. for 1 h. Y is conversion in percent and X is run number.

Recovery and catalyst reuse are important issues and therefore an easy catalyst separation and recycling in successive batch operations can greatly increase the efficiency of the overall process. Running the reaction using the same batch of catalyst, lead to a moderate decrease in reactivity for three consecutive runs. Reactivation of Pd/C after the fifth run with hydrogen proved to be successful to increase catalyst reactivity. See FIG. 3. The reactivation was done by placing the catalyst in ethanol and apply a hydrogen pressure of 5 bar and leave the catalyst there for 12 hours at room temperature. The reactivated catalyst was then rinsed with ethanol.

Example 4

Procedure: 5 g of air dry birch chips was used together with 20 mol % catalyst in respect to lignin content (MW of lignin monomer was assumed to be 243 g/mol, Klasson method). The solvent system used was water/ethanol 1:1, 180 ml. The reaction was performed at 180-190 degrees for 1 h in a sealed high pressure reactor. In all cases the reactor was flushed with nitrogen prior to use. Heating program was the same as in palladium case.

Figure 4:
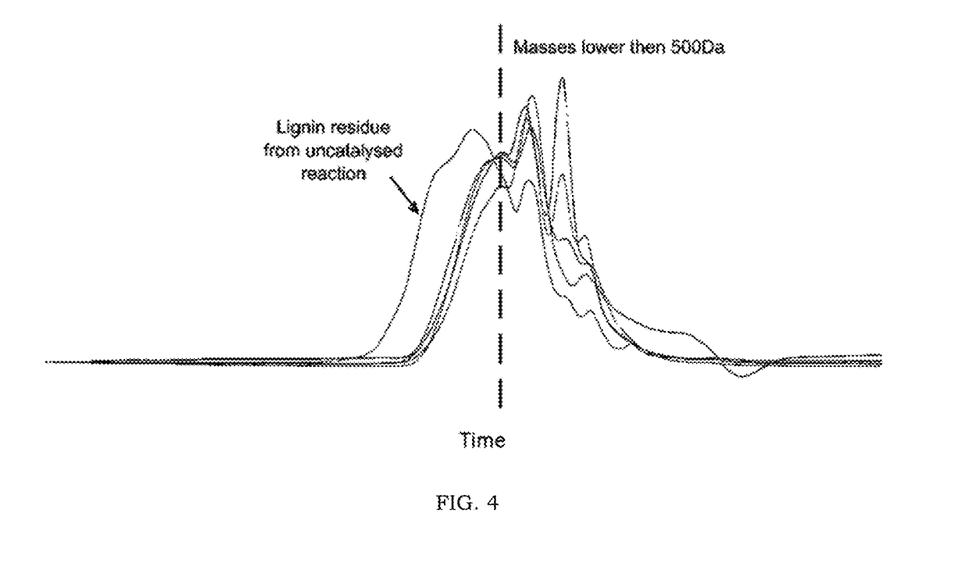
FIG. 4. GPC of the lignin residues from uncatalyzed reaction and from treatments according to the present invention using various catalysts.
Figure 5:
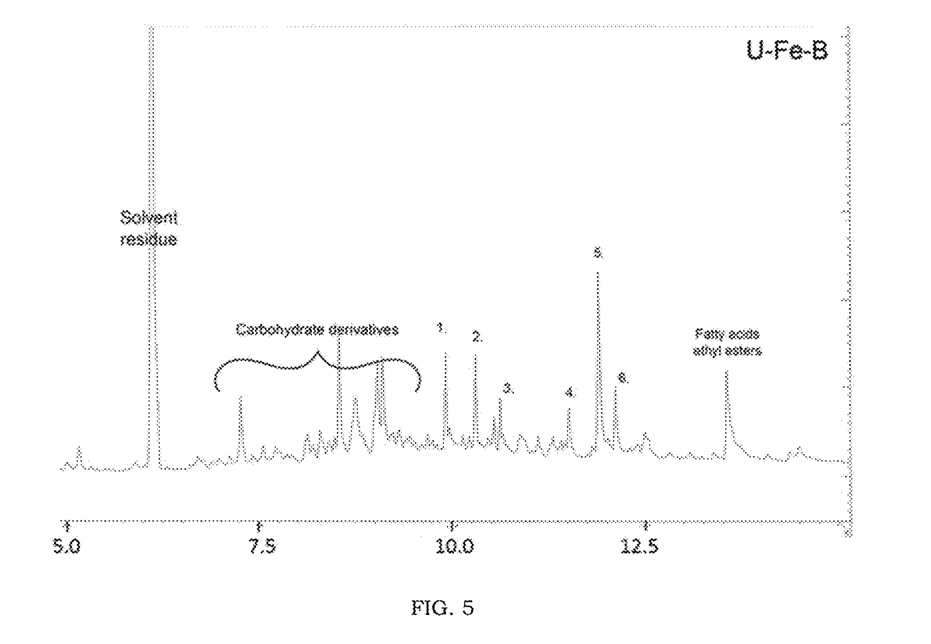
FIG. 5. GC-MS from lignin residues after treatment using U-Fe-B catalyst.
Figure 6:
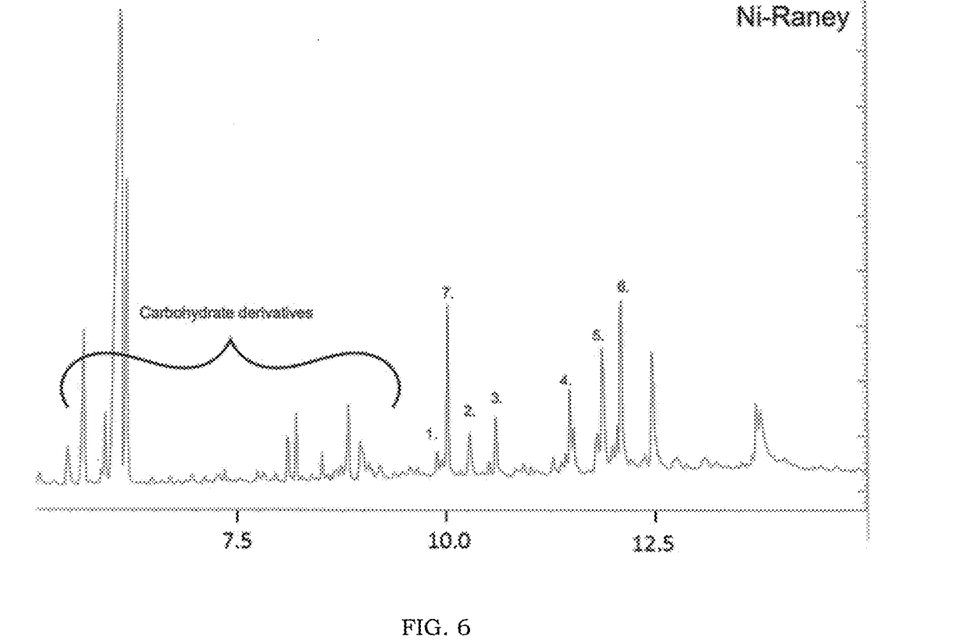
FIG. 6. GC-MS from lignin residues after treatment using Raney Nickel catalyst.
Figure 7:
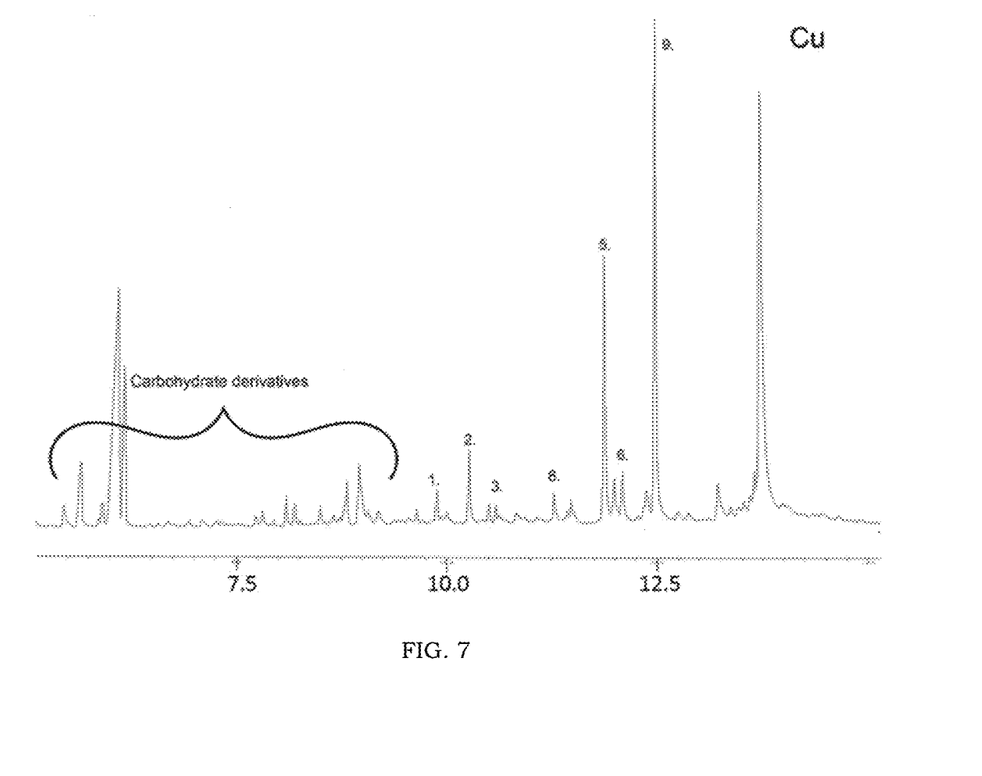
FIG. 7. GC-MS from lignin residues after treatment using Cu catalyst.
Figure 8:
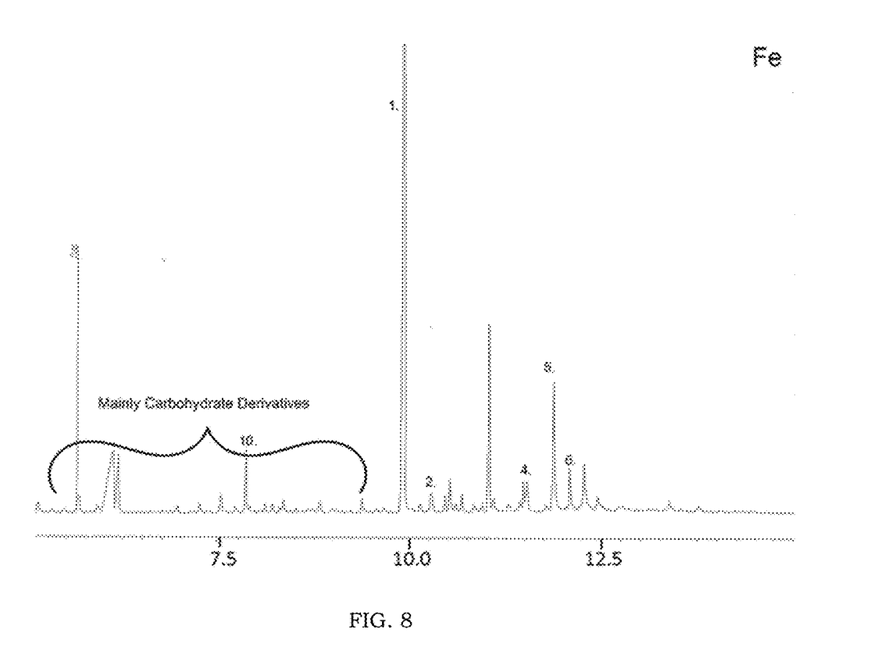
FIG. 8. GC-MS from lignin residues after treatment using Fe catalyst.

Lignin depolymerization catalysed by added metal catalyst. Catalysts used are W/C, Urushibara catalyst U-Fe-B, Cu, Raney Nickel (2800, Sigma Aldrich) and Fe. GPC analysis disclosed a distinct depolymerization for all transition meal catalysts, FIG. 4. GC-MS discloses the lignin residues, FIG. 5-8.

Iron catalyst was prepared by reduction of Iron (II) or (III) source with sodium borohydride in water. The iron catalyst was used directly without prewashing and filtration. U-Fe-B was prepared according to literature procedure. Copper was used as fine metal powder.

Legends for GC-MS
1. 2,6-dimethoxyphenol
2. 4-hydroxy-3-methoxybenzaldehyde
3. 2-methoxy-4-(prop-1-en-1-yl)phenol
4. E/R-2,6-dimethoxy-4-(prop-1-en-1-yl)phenol
5. 4-hydroxy-3,5-dimethoxybenzaldehyde
6. E/R-2,6-dimethoxy-4-(prop-1-en-1-yl)phenol
7. 2-methoxy-4-propylphenol
9. 1-(4-hydroxy-3,5-dimethoxyphenyl)prop-2-en-1-one
10. 2-methoxyphenol

The invention claimed is:

1. A method of depolymerizing lignin comprising:
   a. Providing biomass in particulate form wherein the biomass contains lignin, a solvent mixture comprising an organic solvent and water, and a transition metal catalyst; wherein the biomass is wood in the form of saw dust or wood chips;
   b. Mixing the biomass, the solvent mixture and the transition metal catalyst to obtain a mixture;
   c. Heating the mixture to at least 160° C. and depolymerize the lignin at a pressure of not more than 50 bar without adding hydrogen; and
   d. Optionally isolating the depolymerized lignin; and
   wherein at least 20 weight % of the depolymerized lignin is 2-methoxy-4-(prop-1-enyl)phenol.

2. The method according to claim 1 wherein the transition metal catalyst is based on palladium.

3. The method according to claim 1 wherein the mixture is heated to at least 180° C.

4. The method according to claim 1 wherein the depolymerized lignin has an average molecular weight ($M_w$) of not more than 1500 g/mol.

5. The method according to claim 4 wherein the lignin has an average molecular weight (Mw) of not more than 1000 g/mol.

6. The method according to claim 1 wherein the mixture is heated for at least 15 minutes.

7. The method according to claim 6 wherein the mixture is heated for at least 1 hour.

8. The method according to claim 1 wherein the organic solvent is an alcohol.

9. The method according to claim 8 wherein the alcohol is methanol or ethanol.

10. The method according to claim 1 wherein the concentration of transition metal catalyst is at least 1 mol % based on the lignin content.

11. The method according to claim 10 wherein the concentration of transition metal catalyst is at least 3 mol %.

12. The method according to claim 1 wherein no added base is used.

13. The method according to claim 1 wherein no formic acid or hydride is added.

14. The method according to claim 1 wherein the depolymerization is conducted in air.

15. The method according to claim 1 wherein the pressure is 35 bar or less.

16. A method of producing one or more compounds having the formula of:

wherein each R1 and R2 is H or $OCH_3$ and R3 is $(CH_2)_2CH_3$, $(CH_2)_3OH$ or $(CH)_2CH_3$ comprising:
   a. Providing biomass in particulate form wherein the biomass contains lignin, a solvent mixture comprising an organic solvent and water, and a transition metal catalyst; wherein the biomass is wood in the form of saw dust or wood chips;
   b. Mixing the biomass, the solvent mixture and the transition metal catalyst to obtain a mixture;
   c. Heating the mixture to at least 160° C. and depolymerize the lignin at a pressure of not more than 50 bar without adding hydrogen;
   d. Optionally isolating the one or more compounds produced; and
   wherein at least 20 wt % of the compounds is (2-methoxy-4-(prop-1-enyl)phenol) R1 is H, R2 is $OCH_3$ and R3 is $(CH)_2CH_3$.

17. The method according to claim 16 wherein the pressure is 35 bar or less.

* * * * *